United States Patent [19]

Gurvich et al.

[11] 4,259,534
[45] Mar. 31, 1981

[54] METHOD FOR THE PRODUCTION OF 2,4,6-TRI(3,5-DITERTIARY BUTYL-4-HYDROXYBENZYL) MESITYLENE

[76] Inventors: Yakov A. Gurvich, Sretensky bulvar, 6, kv. 61; Simona T. Kumok, Poklonnaya ulitsa, 4, kv. 32; Galina G. Latysheva, Bolshaya Pereyaslavskaya ulitsa, 6, korpus 2, kv. 156; Anna I. Rybak, Amurskaya ulitsa, 10, korpus 2, kv. 42; Evgeny L. Styskin, Khalturinskaya ulitsa, 10, korpus 2, kv. 42, all of Moscow; Alexandr G. Liakumovich, ulitsa Galeeva, 10, kv. 8, Kazan; Jury I. Michurov, prospekt Lenina 13, kv. 4, Sterlitamak Bashkirskaya ASSR; Rufina A. Filipova, ulitsa Safrazyana, 10; Vladimir A. Yanshevsky, ulitsa Kommunisticheskaya, 42, kv. 12, both of Novokuibyshevsk Kuibyshevskoi oblasti; Grigory I. Rutman, ulitsa Revoljutsionnaya, 17, kv. 6; Igor J. Logutov, prospekt Lenina, 87, kv. 84, both of Sterlitamak Bashkirskaya ASSR, all of U.S.S.R.

[21] Appl. No.: 840,329

[22] Filed: Oct. 7, 1977

[30] Foreign Application Priority Data

Oct. 12, 1976 [SU] U.S.S.R. ............................... 2410436

[51] Int. Cl.$^3$ .............................................. C07C 37/16
[52] U.S. Cl. ..................................................... 568/720
[58] Field of Search ......................................... 568/720

[56] References Cited

U.S. PATENT DOCUMENTS

| 2,779,800 | 1/1957 | Holm et al. | 568/720 |
| 3,026,264 | 3/1962 | Rocklin et al. | 568/730 |
| 3,047,503 | 7/1962 | Jaffe et al. | 568/730 |
| 3,052,728 | 9/1962 | Rocklin | 568/730 |
| 3,309,339 | 3/1967 | Barton et al. | 568/720 |
| 3,644,538 | 2/1972 | Starnes | 568/720 |
| 3,845,142 | 10/1974 | Gurvich et al. | 568/720 |
| 3,925,488 | 12/1975 | Shin | 568/720 |

FOREIGN PATENT DOCUMENTS

| 1910793 | 9/1970 | Fed. Rep. of Germany | 568/730 |
| 1202762 | 8/1970 | United Kingdom . | |

Primary Examiner—Norman Morgenstern
Attorney, Agent, or Firm—Lackenbach, Lilling & Siegel

[57] ABSTRACT

A method for the production of 2,4,6-tri(3,5-ditertiary butyl-4-hydroxybenzyl)mesitylene which resides in treating a mesitylene solution in chloroalkane simultaneously with sulfuric acid used as a catalyst and a solution of 2,6-ditertiary butyl-4-methoxymethylphenol or bis-3,5-ditertiary butyl-4-hydroxybenzyl ether in chloroalkane at a temperature of −20° to +20° C. This results in a reaction mixture consisting of an acid phase and an organic phase including the target product. The phases are separated. The organic phase is subjected to neutralization by the treatment thereof with gaseous ammonia used as an alkaline agent. The precipitate of ammonium sulfate is separated and chloroalkane is removed from the remaining solution.

The proposed method makes it possible to obtain the target product with a yield of 88 to 90% and a melting temperature of 239° to 239.5° C.

The method prevents the formation of effluents, and the amount of phenol wastes is considerably reduced.

4 Claims, No Drawings

METHOD FOR THE PRODUCTION OF 2,4,6-TRI(3,5-DITERTIARY BUTYL-4-HYDROXYBENZYL) MESITYLENE

The present invention relates to methods for the production of 2,4,6-tri (3,5-ditertiary butyl-4-hydroxybenzyl) mesitylene.

Said 2,4,6-tri (3,5-ditertiary butyl-4-hydroxybenzyl) mesitylene is a non-coloring non-toxic and non-volatile effective stabilizing agent of the class of polynuclear phenols for plastics and other organic products, especially those which are processed at elevated temperatures or operate under vacuum and high temperatures. For example, it is widely used for stabilizing polyolefins, polyamides, polyhydroxymethylene, polyacetals, polystyrene, phenolformaldehyde resins, nylon, rubber and other polymeric materials. In particular, cast and extruded articles of natural color or colors in various light shades are made from polyolefins stabilized with 2,4,6-tri (3,5-ditertiary butyl-4-hydroxybenzyl) mesitylene.

2,4,6-tri (3,5-ditertiary butyl-4-hydroxybenzyl) mesitylene is used for stabilizing some medicinal and cosmetic preparations, as well as articles which are in contact with medicinal and food preparations.

There are a number of methods for the production of 2,4,6-tri (3,5-ditertiary butyl-4-hydroxybenzyl) mesitylene. One of the methods consists in reacting mesitylene with 3,5-ditertiary butyl-4-hydroxybenzyl alcohol in a solvent—methylene chloride—in the presence of sulfuric acid according to the formula

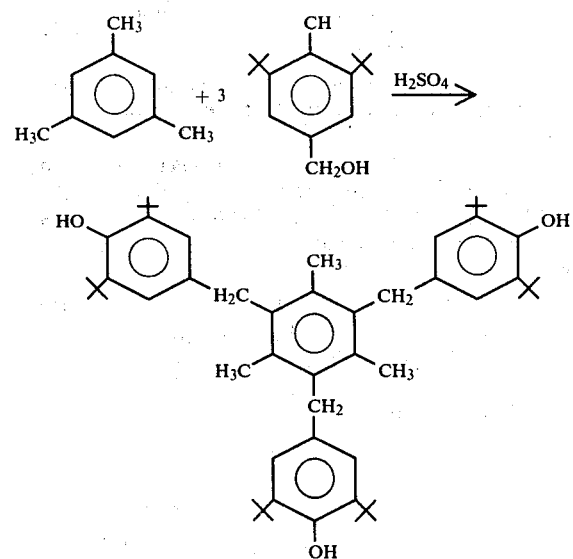

wherein X is $C(CH_3)_3$.

The process is carried out in the following manner: to a solution of 0.4 mole of 3,5-ditertiary butyl-4-hydroxybenzyl alcohol and 0.1 mole of mesitylene in methylene chloride at a temperature of 4° C. there is added 6.5 moles of 80% sulfuric acid for 30 minutes. The resultant reaction mixture is stirred for three more hours after which it is washed 4 times with water to a neutral reaction. Methylene chloride is then distilled off and the target product is crystallized from the remaining mass, which product is further recrystallized from isopentane. After recrystallization a product is obtained having a melting temperature of 200° to 200.7° C. The yield of the product is 60% as calculated for the alkylating agent.

In effecting this method a large amount of acidic effluents is formed which contain organic solvents and phenols. The purification of such effluents involves considerable difficulties.

Said method requires a considerable amount of sulfuric acid and an alkylating agent, the yield of the target product being insufficiently high. In addition, the degree of purity of the product being obtained is also insufficient, therefore an additional recrystallization of the product is required. This results in a more complicated technology of the method and a lower yield of the product. The alkylating agent employed in this method—3,5-ditertiary butyl-4-hydroxybenzyl alcohol—is not readily available. Its synthesis is accompanied with formation of a large amount of byproducts which results in its low yield.

Known in the art is another method for the production of 2,4,6-tri (3,5-ditertiary butyl-4-hydroxybenzyl) mesitylene by reacting mesitylene and an ester of 3,5-ditertiary butyl-4-hydroxybenzyl alcohol. Said alkylating agent and mesitylene are dissolved in methylene chloride and 80% sulfuric acid is added at a temperature of 3° C. in a flow of nitrogen at a rate of 0.5 to 2 moles of acid per one mole of mesitylene. The resultant reaction mixture is stirred for 3 hours at a temperature of 10° to 40° C. Then isooctane is added thereto, the aqueous layer is separated, and the organic layer is washed with water, then with a 15% ammonia solution and again with water. Thereafter methylene chloride is distilled off from the organic layer.

The yield of the target product is 78 to 79% as calculated for the alkylating agent—a 3,5-ditertiary butyl-4-hydroxybenzyl alcohol ester.

The main disadvantages of this method are the formation of a large amount of effluents containing an acid, organic solvents and, phenols, and a low yield of the target product.

The most perfect method is the production of 2,4,6-tri(3,5-ditertiary butyl-4-hydroxybenzyl) mesitylene by alkylation of mesitylene with ethers of 3,5-ditertiary butyl-4-hydroxybenzyl alcohol, particularly, with 2,6-dithertiary butyl-4-methoxymethylphenol or with a bis-3,5-ditertiary butyl-4-hydroxybenzyl ether in a solvent—chloroalkane. According to this method, the process of reaction of reagents is carried out with a gradual feeding of the catalyst—sulfuric acid—to a mixture of reagents at a temperature of −20° to +20° C. The resultant reaction mixture is separated from the acid and neutralized with an alkaline agent—sodium hydroxide in the form of a 5 to 7% aqueous solution. Thereafter the aqueous phase is separated and the solvent is distilled off from the organic phase.

The yield of the target product is 60 to 67% of the theoretical as calculated for the alkylating agent.

The degree of purity of the product is higher than in the previously described methods (the melting temperature is 238° to 239° C.). This precludes the necessity of additional recrystallization.

However, the disadvantages of this method are the formation of a large amount of effluents, and an insufficiently high yield of the target product due to the alkylating agent being taken with an excess of 25% (4 moles instead of 3 moles of the theoretical per one mole of mesitylene). In carrying out the process this excess is required for obtaining the target product with a high degree of purity practically containing no impurity of 2,4-di(3,5-ditertiary butyl-4-hydroxybenzyl) mesitylene. However, over 20% of 2,6-ditertiary butyl-4-methoxymethylphenol or bis-3,5-ditertiary butyl-4-hydroxybenzyl ether is converted into a byproduct—4,4-methylene bis-(2,6-ditertiary butyl phenol). The washing off of this impurity from the target product results in a reduction of the yield thereof and requires high consumption of methanol for washing.

It is an object of the present invention to provide such method for the production of 2,4,6-tri(3,5-ditertiary butyl-4-hydroxybenzyl) mesitylene which would make it possible to obtain said product with a sufficiently high yield and a sufficiently high degree of purity.

It is another object of the present invention to preclude the formation of effluents.

In accordance with the above and other objects the invention resides in a method for the production of 2,4,6-tri(3,5-ditertiary butyl-4-hydroxybenzyl) mesitylene by reacting mesitylene with 2,6-ditertiary butyl-4-methoxymethylphenol or bis-3,5-ditertiary butyl-4-hydroxybenzyl ether at a temperature of −20° to +20° C. in the presence of a solvent—chloroalkane, and a catalyst—sulfuric acid to produce a reaction mixture comprising an acid phase and an organic phase containing the target product, with subsequent separation of said phases, treatment of the organic phase with an alkaline agent and subsequent separation of the target product by removing the solvent. According to the invention, the mesitylene solution in chloroalkane is simultaneously treated with sulfuric acid and a solution of 2,6-ditertiary butyl-4-methoxymethylphenol or bis-3,5-ditertiary butyl-4-hydroxybenzyl ether in chloroalkane, and the alkaline agent is gaseous ammonia. After the treatment therewith of the organic phase prior to the separation of the target product, the resultant ammonium sulfate is separated.

Methylene chloride, carbon tetrachloride and dichloroethane can be used as the solvent—chloroalkane.

As pointed out above, it is advisable to carry out the process within −20° to +20° C. If the temperature is lower than said lower limit the alkylation reaction is greatly retarded and the duration of the process gets longer. An increase in the temperature of more than 20° C. results in a sharp increase in the formation of byproducts.

Under the above conditions mesitylene is alkylated with 2,6-ditertiary butyl-4-methoxymethylphenol according to the formula:

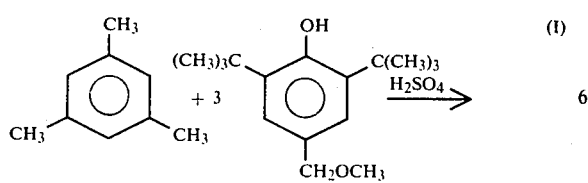

(I)

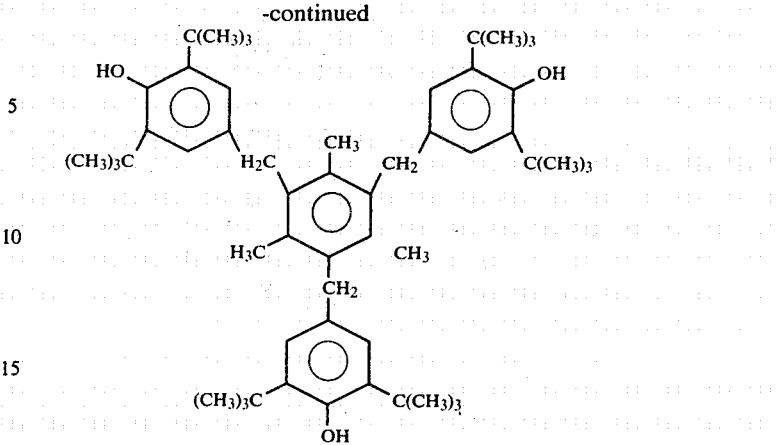

The excess of the alkylating agent leads to the formation of a byproduct—4,4-methylene bis (2,6-ditertiary butylphenol) according to the formula

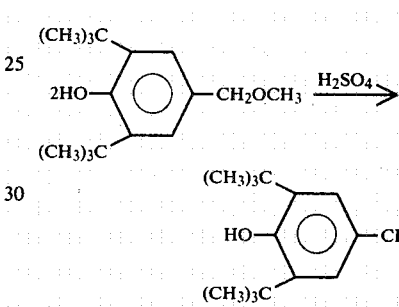

(II)

In addition, an increase in the temperature of more than 20° C. is conducive to the formation of said byproduct.

A decrease in the amount of the alkylating agent lower than the stoichiometric results in the formation of another byproduct—2,4-di(3,5-ditertiary butyl-4-hydroxybenzyl) mesitylene

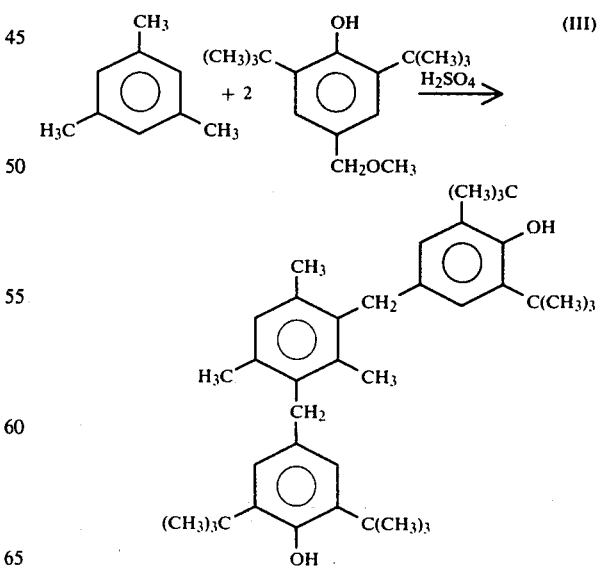

(III)

In case of employing bis- 3,5-ditertiary butyl-4-hydroxybenzyl ether as the alkylating agent under the above-mentioned conditions byproducts II and III are also formed.

As compared to the methods known in the prior art the proposed method makes it possible to obtain 2,4,6-tri(3,5-ditertiary butyl-4-hydroxybenzyl) mesitylene with a sufficiently high yield of the order of 88 to 90% and a sufficiently high degree of purity (the melting temperature is 239° to 239.5° C). In effecting the proposed method an insignificant amount of the alkylating agent and sulfuric acid is required which ensures a sharp drop in the amount of phenol wastes forming in the prior art methods. The use of gaseous ammonia as an alkaline agent prevents the formation of effluents.

The method is technologically simple and is effected in the following manner.

A portion of the required amount of chloroalkane and mesitylene is placed in a flask provided with an agitator, a thermometer, a cooler, two dropping funnels, and a bath for cooling. The content of the flask is cooled to the desired temperature. Then an alkylating agent solution in the second portion of chloroalkane and sulfuric acid are simultaneously added while stirring. The process temperature is maintained wihin the range of $-20°$ to $+20°$ C. The resultant mass represents an acid and an organic phase. The acid phase is separated in the dividing funnel, and the organic phase containing the target product is placed in a flask provided with an agitator, a reflux condenser, and a gas-supplying tube, and treated with gaseous ammonia. The resultant ammonia sulfate is separated by filtration and the solvent—chloroalkane—is distilled off from the remaining solution.

For a better understanding of the present invention the following specific examples are presented below.

EXAMPLE 1

To a flask provided with an agitator, a thermometer, a reflux condenser and two dropping funnels, there are loaded 100 ml of methylene chloride and 6.84 g (0.057 mole) of mesitylene. The mixture is cooled to 0° C. while stirring. To the resultant mixture there are simultaneously added 21 g (0.2 mole) of sulfuric acid and a solution of 50 g (0.2 mole) of 2,6-ditertiary butyl-4-methoxymethylphenol in 100 ml of methylene chloride for 30 to 40 minutes maintaining a temperature of 0° to 3° C.

The reaction mixture is then agitated at this temperature for another 30 minutes. The composition of the reaction mixture is analyzed by a method of gas-liquid chromatography.

The composition of the reaction mixture in percent by weight:
product I: 94.2;
product II: 5.1;
product III: 0.7.

The reaction mixture is placed in a dividing funnel and the acid phase is separated. The organic phase is placed in a flask provided with an agitator, a reflux condenser, and a gas-supplying tube through which gaseous ammonia is fed for neutralization. The resultant ammonium sulfate is separated by filtration. Methylene chloride is distilled off from the remaining solution.

39.1 g of the target product is obtained which is 88.6% of the theoretical as calculated for mesitylene, or 76.1% of the theoretical as calculated for 2,6-ditertiary butyl-4-methoxymethylphenol. The melting temperature is 239.1° to 239.6° C.

The following experiment was conducted for comparison.

Into a flask provided with an agitator, a thermometer, a reflux condenser and a dropping funnel, there was loaded 200 ml of methylene chloride, 6.02 g (0.05 mole) of mesitylene, and 43.75 g (0.17 mole) of 2,6-ditertiary butyl-4-methoxymethylphenol. The mixture is cooled to 0° C. while stirring, and 18.25 g (0.17 mole) of sulfuric acid is gradually added for 30 minutes, maintaining a temperature of 0° to 3° C.

Then the reaction mixture is agitated for another 30 minutes at the same temperature.

The composition of the reaction mixture in percent by weight:
product I: 75.2;
product II: 15.2;
product III: 9.6.

The reaction mixture is then neutralized with a 7% sodium hydroxide solution, the aqueous layer is separated and the solvent is distilled off from the organic layer. 28.2 g of the target product is obtained which constitutes 72.9% of the theoretical as calculated for mesitylene.

The melting temperature is 238.6° to 239.2° C.

It can be seen from the above data that with simultaneous loading of the components into the reaction zone the yield of the target product and the degree of its purity sharply drop due to the formation of a considerable amount of byproducts.

EXAMPLE 2

Into the flask of Example 1 there are loaded 100 ml of methylene chloride and 7.2 g (0.06 mole) of mesitylene. The mixture is cooled to 0° C. while stirring. To the resultant mixture there are simultaneously added 21 g (0.2 mole) of 94% sulfuric acid and a solution of 50 g (0.2 mole) of 2,6-ditertiary butyl-4-methoxymethylphenol in 100 ml of methylene chloride for 30 to 40 minutes maintaining a temperature of 0° to 3° C. The reaction mixture is then agitated at the same temperature for another 30 minutes. The composition of the reaction mixture is analyzed by a method of gas-liquid chromatography.

The composition of the reaction mixture in percent by weight:
product I: 94.0;
product II: 3.8;
product III: 2.2.

The separation of the organic and the acid phase, neutralization of the organic phase with gaseous ammonia, the distillation of the solvent and the separation of the product are effected as in Example 1.

The yield of the target product is 41.4 g which is 89.1% of the theoretical as calculated for mesitylene, or 80.2% of the theoretical as calculated for the alkylating agent. The melting temperature is 239.2° to 239.8° C.

The following experiment was conducted for comparison.

Into a flask provided with an agitator, a thermometer, a reflux condenser, and a dropping funnel there were loaded 200 ml of methylene chloride, 50 g (0.2 mole) of 2,6-ditertiary butyl-4-methoxymethylphenol and 6.02 g (0.05 mole) of mesitylene. The mixture was cooled while stirring to 0° C. and 22 g of 94% (0.2 mole) sulfuric acid was gradually added for 30 minutes maintaining a temperature of 0° to 3° C. The reaction mixture was then agitated for another 30 minutes at the same temperature.

The composition of the reaction mixture in percent by weight:

product I: 79.5;
product II: 3.3;
product III: 17.2.

The reaction mixture was neutralized with a 7% solution of NaOH, the aqueous layer was separated, and the solvent was distilled off from the organic layer.

The yield of the product is 30.7 g which is 79.3% of the theoretical as calculated for mesitylene, or 59.5% as calculated for 2,6-ditertiary butyl-4-methoxymethylphenol. The melting temperature of the obtained product is 238.0° to 238.7° C.

EXAMPLE 3

Into the flask of Example 1 there are loaded 13 ml of methylene chloride and 1.03 g (0.0086 mole) of mesitylene. The mixture is cooled to 0° C. while stirring and there are simultaneously added 2.71 g of 94% (0.026 mole) sulfuric acid and a solution of 6.5 g (0.026 mole) of 2,6-ditertiary butyl-4-methoxymethylphenol in 13 ml of methylene chloride maintaining a temperature of 0° to 3° C. The reaction mixture is agitated at the same temperature for another 30 minutes. The composition of the reaction mixture is analyzed by a method of gas-liquid chromatography.

The composition of the reaction mixture in percent by weight:
product I: 91.7;
product II: 1.7;
product III: 6.6.

The reaction mixture is treated and the target product is separated as in Example 1.

5.4 g of the target product is obtained which is 81.5% of the theoretical as calculated for mesitylene, or 81.0% of the theoretical as calculated for 2,6-ditertiary butyl-4-methoxymethylphenol. The melting temperature is 239.0° to 239.6° C.

EXAMPLE 4

Into the flask of Example 1 there are loaded 13 ml of methylene chloride and 1.11 g (0.0093) mole of mesitylene. The mixture is cooled to 0° C. while stirring and there are simultaneously added 2.71 g (0.026 mole) of 94% sulfuric acid and a solution of 6.5 g (0.026 mole) of 2,6-ditertiary butyl-4-methoxymethylphenol in 13 ml of methylene chloride maintaining a temperature of 0° to 3° C.

The reaction mixture is then stirred at the same temperature for another 30 minutes.

The composition of the reaction mixture in percent by weight:
product I: 80.5;
product II: 1.2;
product III: 18.3.

The reaction mixture is treated and the target product is separated as in Example 1.

5.1 g of the target product is obtained which is 70.9% of the theoretical as calculated for mesitylene, or 76.0% of the theoretical as calculated for 2,6-ditertiary butyl-4-methoxymethylphenol. The melting temperature is 238.9° to 239.4° C.

EXAMPLE 5

Into the flask of Example 1 there are loaded 100 ml of methylene chloride and 7.2 g (0.06 mole) of mesitylene. The mixture is cooled to 0° C. while stirring. To the resultant mixture there are simultaneously added a solution of 45 g (0.099 mole) of bis-3,5-ditertiary butyl-4-hydroxybenzyl ether in 100 ml of methylene chloride and 8 g (0.08 mole) of 94% sulfuric acid, maintaining a temperature of 0° to 3° C. The reaction mixture is then stirred at the same temperature for another 30 minutes.

The composition of the reaction mixture in percent by weight:
product I: 93.8;
product II: 3.7;
product III: 2.5.

The reaction mixture is treated and the target product is separated as in Example 1.

The yield of 2,4,6-tri(3,5-ditertiary butyl-4-hydroxybenzyl) mesitylene is 40.5 g which is 87.2% of the theoretical as calculated for mesitylene, or 79.2% of the theoretical as calculated for ether. The melting temperature is 239.4° to 239.8° C.

The following experiment was carried out for comparison.

Into the flask of Example 1 there were loaded 12 ml of methylene chloride, 2.70 g (0.006 mole) of bis-3,5-ditertiary butyl-4-hydroxybenzyl ether and 0.4 g (0.003 mole) of mesitylene. The mixture was cooled while stirring to 0° C. and 1.22 g (0.012 mole) of 94% sulfuric acid was gradually added for 60 minutes, maintaining a temperature of 0° to 3° C.

The reaction mixture was then stirred for another 30 minutes at the same temperature.

The composition of the reaction mixture in percent by weight:
product I: 82.0;
product II: 15.5;
product III: 2.5.

1.86 g of the target product was obtained which is 80.2% of the theoretical as calculated for mesitylene.

EXAMPLE 6

Into the flask of Example 1 there are loaded 100 ml of methylene chloride and 7.2 g (0.06 mole) of mesitylene. The mixture is cooled, while stirring, to −20° C. and a solution of 50 g (0.2 mole) of 2,6-ditertiary butyl-4-methoxymethylphenol in 100 ml of methylene chloride and 21 g (0.2 mole) of sulfuric acid are simultaneously added for 30 minutes, maintaining a temperature of −20° C. The reaction mixture is stirred for 120 minutes at the same temperature and a sample is taken for analysis.

The composition of the reaction mixture in percent by weight:
product I: 82.0;
product II: 5.6;
product III: 12.4.

The reaction mixture is treated and the target product is separated as in Example 1. 34.8 g of the target product is obtained which is 75% of theoretical as calculated for mesitylene, or 68.0% of the theoretical as calculated for the alkylating agent.

The melting temperature is 238.6° to 239.3° C.

EXAMPLE 7

Into the flask described above there are loaded 100 ml of dichloroethane and 7.2 g (0.06 mole) of mesitylene. The mixture is cooled while stirring to 12° C. and a solution of 50 g (0.2 mole) of 2,6-ditertiary butyl-4-methoxymethylphenol in 100 ml of dichloroethane and 21 g (0.02 mole) of sulfuric acid are gradually added for 30 minutes maintaining a temperature of 12° C. The reaction mixture is further stirred for 60 minutes at the same temperature and a sample is taken for analysis.

The composition of the reaction mixture in percent by weight:
product I: 83.8;
product II: 9.7;
product III: 6.5.

The reaction mixture is treated and the target product is separated as in Example 1.

35.2 g of the target product is obtained which is 75.8% of the theoretical as calculated for mesitylene, or 68.5% of the theoretical as calculated for 2,6-ditertiary butyl-4-methoxymethylphenol.

The melting temperature is 238.9° to 239.3° C.

EXAMPLE 8

Into the flask of Example 1 there are loaded 100 ml of carbon tetrachloride and 7.2 g (0.06 mole) of mesitylene. The mixture is stirred and a solution of 50 g (0.2 mole) of 2,6-ditertiary butyl-4-methoxymethylphenol in 100 ml of carbon tetrachloride and 21 g (0.2 mole) of sulfuric acid are gradually added at the same time at a temperature of 20° C. for 30 minutes maintaining a temperature of 20° C. The reaction mixture is further stirred for 30 minutes at the same temperature, and a sample is taken for analysis.

The composition of the reaction mixture in percent by weight:
product I: 87.2;
product II: 8.7;
product III: 4.1.

37.4 g of the target product is obtained which is 80.5% of the theoretical as calculated for mesitylene, or 73.0% of the theoretical as calculated for the alkylating agent.

The melting temperature is 238.0° to 238.7° C.

We claim:

1. A method for the production of 2,4,6-tri(3,5-ditertiary butyl-4-hydroxybenzyl)mesitylene residing in treating a mesitylene solution in a chloroalkane simultaneously with sulfuric acid used as a catalyst, and a solution of 3,5-ditertiary butyl-4-hydroxybenzyl alcohol ether selected from the group consisting of 2,6-ditertiary butyl-4-methoxymethylphenol and bis-3,5-ditertiary butyl-4-hydroxybenzyl ether, in said chloroalkane at a temperature of −20° to +20° C. to produce a reaction mixture consisting of an acid phase and an organic phase including the target product; separating said phases; neutralizing the organic phase by the treatment thereof with gaseous ammonia used as an alkaline agent to form ammonium sulfate; separating ammonium sulfate; distilling off the chloroalkane from the remaining solution.

2. The method of claim 1 wherein said chloroalkanes are selected from the group consisting of methylene chloride, carbon tetrachloride, and dichloroethane.

3. The method of claim 1 wherein said hydroxybenzyl ether is 2,6-ditertiary butyl-4-methoxymethylphenol.

4. The method of claim 1 wherein said hydroxybenzyl ether is bis-3,5-ditertiary butyl-4-hydroxybenzyl ether.

* * * * *